United States Patent [19]

Mueller et al.

[11] Patent Number: 4,973,769
[45] Date of Patent: Nov. 27, 1990

[54] PREPARATION OF 1,2,4-BUTANETRIOL

[75] Inventors: Herbert Mueller, Frankenthal; Walter Mesch, Ludwigshafen; Klaus Broellos, Seeheim-Jugenheim, all of Fed. Rep. of Germany

[73] Assignee: BASF Aktiengesellschaft, Ludwigshafen, Fed. Rep. of Germany

[21] Appl. No.: 306,309

[22] Filed: Feb. 3, 1989

[30] Foreign Application Priority Data

Feb. 6, 1988 [DE] Fed. Rep. of Germany ....... 3803581

[51] Int. Cl.$^5$ ..................... C07C 29/136; C07C 31/22
[52] U.S. Cl. .................................................. 568/864
[58] Field of Search ........................................ 568/864

[56] References Cited

U.S. PATENT DOCUMENTS

| 4,009,124 | 2/1977 | Laurer et al. | 252/463 |
| 4,268,695 | 5/1981 | Lange et al. | 568/864 |
| 4,410,744 | 10/1983 | Campbell et al. | 568/864 |
| 4,594,462 | 6/1986 | Schnabel et al. | 568/864 |
| 4,656,297 | 4/1987 | Kouba et al. | 568/864 |

FOREIGN PATENT DOCUMENTS

| 2445303 | 4/1976 | Fed. Rep. of Germany . |
| 2643400 | 3/1978 | Fed. Rep. of Germany . |
| 59-70632 | 4/1984 | Japan . |

OTHER PUBLICATIONS

The Journal of the American Chemical Society, 70 (1948), 3121-25.

Primary Examiner—J. E. Evans
Attorney, Agent, or Firm—Keil & Weinkauf

[57] ABSTRACT 1,2,4-Butanetriol is prepared by catalytic hydrogenation of malic esters over a copper-containing catalyst by passing the esters over the fixed-bed catalyst at from 130° to 190° C. under hydrogen partial pressures of from 100 to 300 bar while substantially avoiding the formation of a gas phase.

2 Claims, No Drawings

PREPARATION OF 1,2,4-BUTANETRIOL 1,2,4-Butanetriol is a useful intermediate for manifold applications. However, since only very complicated and expensive methods have been disclosed for preparing said triol, it has not become as widely established as, for example, glycerol. It is used as a building block in the syntheses of active substances and for preparing nitrates for particular explosives.

1,2,4-Butanetriol is obtained by hydrating 2-butyne-1,4-diol by means of mercury catalysts. For reasons of occupational hygiene, this reaction is not suitable for the industrial production of the triol. It is more advantageous to hydrogenate 2-butene-1,4-diol epoxide to 1,2,4-butanetriol as described in German Published Application DAS No. 2,643,400 and Japanese Preliminary Published Application No. 59/70,632. The epoxide is obtained by reacting butenediol with hydrogen peroxide. A low-selectivity dehydration reaction on the 1,3-butanediol gives 3-buten-1-ol which, by subsequent hydroxylation with hydrogen peroxide over a tungsten catalyst in aqueous solution, gives the triol.

U.S. Pat. No. 4,410,744 proposes that 2,3-epoxy-1-propanol (glycide) be subjected to a hydroformylation reaction and the oxo product obtained be converted catalytically with hydrogen or with hydrides into 1,2,4-butanetriol. This synthesis, too, requires a comparatively costly starting material and multiple reaction steps. In said patent it is pointed out that 1,2,4-butanetriol has previously only been prepared on a laboratory scale by hydrogenation of malic acid or an ester thereof. This laboratory method is described in J. Amer. Chem. Soc. 70 (1948), 3121-25. Using this method it is possible to hydrogenate diethyl malate with 1.5 times the amount of a copper chromite catalyst, based on the ester, to give 1,2,4-butanetriol in a 50-70% yield. It is expressly pointed out that this high selectivity combined with a sufficiently high rate of reaction is only obtainable with excess catalyst. At lower catalyst concentrations it is necessary to maintain a higher reaction temperature, correspondingly reducing the selectivity.

Since malic acid is easy to prepare by hydrating maleic acid, it is an object of the present invention to develop a process whereby 1,2,4-butanetriol is preparable on the basis of maleic acid not only in the laboratory but also on an industrial scale. More particularly, the object is to hydrogenate malic acid or an ester thereof to butanetriol economically, even with low catalyst quantities.

We have found that this object is achieved in a particularly advantageous manner with a process for preparing 1,2,4-butanetriol by catalytic hydrogenation of a malic ester over a copper-containing catalyst at elevated temperature under superatmospheric pressure by passing the malic ester at from 130° to 190° C. under a hydrogen partial pressure of from 100 to 300 bar over the fixed-bed catalyst while substantially avoiding the formation of a gas phase.

The malic esters suitable for the hydrogenation are derived from alcohols of from 1 to 8 carbon atoms. It is possible to use aliphatic or cycloaliphatic alcohols for forming the ester, such as methanol, ethanol, propanol, butanol, 2-ethylhexanol and cyclohexanol. Preference is given to alcohols having a branched carbon chain. The most suitable starting materials have proved to be the diisopropyl ester and in particular the diisobutyl ester.

The malic esters can be used for the hydrogenation in pure form or as dilute solutions. Suitable solvents are for example open-chain or cyclic ethers, such as diethyl ether or tetrahydrofuran, aliphatic and aromatic hydrocarbons, which may contain for example 5 to 10 carbon atoms, other solvents which are inert under the hydrogenation conditions, and in particular also alcohols, in which case it is advantageous to use those alcohol solvents which were used to prepare the malic ester. If solutions of malic esters are used for the hydrogenation, the solvent content is for example up to 90% by weight. Advantageously, solutions having an ester content of 20 to 80, in particular from 30 to 70, % by weight are used.

According to the invention, the hydrogenation of the malic ester is carried out by the liquid-phase procedure. In this procedure, the starting material in liquid form, or the solution of starting material, is passed for example upward or downward over the catalyst disposed in the hydrogenation reactor as a fixed bed covered by liquid with essentially no free gas space.

Hydrogenation is effected in the presence of copper-containing catalysts of the type customary for carboxylic ester hydrogenation. These catalysts usually contain, besides copper, chromium as an active hydrogenating metal, such as Adkins catalysts, which contain chromium and copper in approximately equimolar amounts, or the catalysts described in German Published Application DAS No. 1,159,925, where the chromium content is much reduced. In addition to copper the catalysts can also contain other hydrogenating metals, such as iron, nickel, cobalt, platinum, palladium, manganese, molybdenum, tungsten or vanadium, although the level of these additives in the catalyst should advantageously not exceed 2% by weight. The copper can have been applied to a suitable carrier, such as aluminum oxide, silica gel, pumice or magnesium silicate, or can have been suitably coprecipitated together with the carrier and subsequently brought into the desired form. A particularly advantageous and hence preferred catalyst, which contains aluminum as well as copper, is described in German Laid-Open Application DOS No. 2,445,303, which is equivalent to U.S. Pat. No. 4,009,124, and which catalyst is formed by precipitating, at a pH of 8 to 9.5 and at a temperature of from 60° to 90° C., a. an aqueous dilute solution of copper and aluminum salts capable of being precipitated by carbonate, the copper and aluminum being present in said solution in an atomic ratio of m:6, m being a number between 2 and 6, with b. an aqueous alkali metal carbonate or bicarbonate solution, the atomic contration of alkali being about twice the concentration of copper and aluminum in said solution, whereby a composition is obtained of the formula $Cu_mAl_6(CO_3)_{0.5m}O_3\text{-}(OH)_{m+12}$, having the above definition, and thereafter drying and annealing the precipitate at 350° to 600° C.

For liquid-phase procedure fixed-bed catalysis according to the invention, the catalysts are shaped into solid structures in a conventional manner. Suitable shapes are for example balls, tablets, rings or even simple extrudates. These are arranged in a suitable pressure-resistant apparatus in the form of a fixed bed which, during the hydrogenation, is permeated by a continuous liquid front comprising feed and product. At the reaction temperature and under the reaction pressure the hydrogen required for the hydrogenation is in a state of solution or suspension (in the form of microbubbles) in the liquid. It is not necessary to maintain a complicated hydrogen recycle during the hydrogenation. As a result, the process according to the invention is particularly economical, since there is no need for a recycle gas pump as used in conventional ester hydrogenation.

Hydrogenation is carried out at from 130° to 190° C., preferably at from 140° to 160° C., under a hydrogen pressure of 100 to 350, preferably from 200 to 300, bar.

The liquids used for the hydrogenation should be substantially acid-free. If they should nonetheless contain acids, it is advisable to neutralize these acids by addition of an inorganic base, such as sodium hydroxide, sodium bicarbonate, sodium carbonate or calcium hydroxide, or alternatively potassium methylate.

With the process according to the invention, a comparatively high rate of reaction is obtained at a comparatively low reaction temperature. A further advantage is that a high conversion is obtained together with a comparatively low proportion of byproducts. It is surprising that the process of the invention gives such advantageous results, since conventional teaching has it that ester hydrogenations are best performed by the trickle-bed technique, as described for example in German Published Application DAS No. 1,159,925 (see column 1 lines 1 to 6 and column 2 lines 40 to 49). If, however, the malic ester is hydrogenated by the trickle-bed technique, hydrogenation to give 1,2,4-butanetriol is possible only with such a substantially lower throughput as to rule out this procedure from use in industry.

In the Example, the parts are by weight and they bear the same relation to parts by volume as the kilogram to the liter.

EXAMPLE 1,000 parts by volume of the copper- and aluminum-containing catalyst obtainable as described in Example 1 of German Laid-Open Application DOS No.2,445,303 are introduced in the form of cylindrical tablets 3 mm in height and 3 mm in diameter into a shaft furnace. The length:diameter ratio of the shaft furnace is 28:1. Before the start of the hydrogenation, during the heating-up phase, isobutanol is passed through the shaft furnace and hydrogen is injected up to a pressure of 10 bar in order first to reduce the catalyst carefully only in the presence of pure isobutanol. The hydrogen pressure is then slowly raised from 10 to 250 bar. At 150° C. the reduction of the catalyst starts, indicated by a marked exothermic reaction. As soon as this exothermic reaction has ceased and substantially all the water of reduction has been discharged, the temperature is raised to 160° C. and a hydrogen pressure of 250 bar is established. The isobutanol feed is then replaced by a 30% strength solution of diisobutyl malate in isobutanol. At 160° C. the oven is charged with 900 parts by volume of the ester solution per hour. At the same time, 2,000 parts by volume of the reactor discharge are kept in circulation by continuous recycling. This serves to dissipate the heat of reaction and to keep the reactor under essentially isothermal conditions. During the hydrogenation 50 parts by volume (S.T.P.) of hydrogen are removed from the furnace per hour. The output from the reaction is 900 parts per hour of the following composition:

86% by weight of isobutanol
2% by weight of 1,4-butanediol
0.2% by weight of diisobutyl succinate
0.5% by weight of 1,2-butanediol
1% by weight of diisobutyl malate
0.2% by weight of monoisobutyl malate
10% by weight of 1,2,4-butanetriol.

On fractional distillation of the mixture, colorless 1,2,4-butanetriol of 99.8% purity is obtained under reduced pressure.

The triol is obtained in a yield of 60% of theory but with about twice the throughput on using for the hydrogenation a 60% strength by weight solution of diisobutyl malate in isobutanol and performing the hydrogenation at 170° C.

We claim:

1. A process for preparing 1,2,4-butanetriol by catalytic hydrogenation of a malic ester over a copper-containing catalyst at elevated temperature under superatmospheric pressure, which comprises passing the malic ester at from 130° to 190° C. under a hydrogen partial pressure of from 100 to 300 bar over the fixed-bed catalyst by the liquid-phase procedure while substantially avoiding the formation of a gas phase, said catalyst being formed by precipitating at pH 8 to 9.5 and a temperature of from 60° to 90° C., a. an aqueous dilute solution of copper and aluminum salts capable of being precipitated by carbonate, the copper and aluminum being present in said solution in an atomic ratio of m:6, m being a number between 2 and 6, with b. an aqueous alkali metal carbonate or bicarbonate solution, the atomic concentration of alkali being about twice the concentration of copper and aluminum in said solution, whereby a composition is obtained of the formula $Cu_mAl_6(CO_3)_{0.5m}O_3\text{-}(OH)_{m+12}$, having the above definition, and thereafter drying and annealing the precipitate at 350° to 600° C.

2. The process of claim 1, wherein the malic ester used is the diisopropyl ester or the diisobutyl ester.

* * * * *